United States Patent
Schlack et al.

(10) Patent No.: US 11,654,084 B2
(45) Date of Patent: May 23, 2023

(54) POUCH COMPRISING A SHAPE MEMORY MATERIAL TO CONTAIN A BIOPHARMACEUTICAL FLUID

(71) Applicant: SARTORIUS STEDIM FMT SAS, Aubagne (FR)

(72) Inventors: Stefan Schlack, Göttingen (DE); Jean-Marc Cappia, Gemenos (FR)

(73) Assignee: SARTORIUS STEDIM FMT SAS, Aubagne (FR)

( * ) Notice: Subject to any disclaimer, the term of this patent is extended or adjusted under 35 U.S.C. 154(b) by 840 days.

(21) Appl. No.: 16/307,738

(22) PCT Filed: Jun. 30, 2017

(86) PCT No.: PCT/EP2017/066384
§ 371 (c)(1),
(2) Date: Dec. 6, 2018

(87) PCT Pub. No.: WO2018/007267
PCT Pub. Date: Jan. 11, 2018

(65) Prior Publication Data
US 2019/0307642 A1    Oct. 10, 2019

(30) Foreign Application Priority Data

Jul. 7, 2016    (EP) .................................... 16315004

(51) Int. Cl.
*A61J 1/10* (2006.01)
*A61J 1/14* (2023.01)
(Continued)

(52) U.S. Cl.
CPC .............. *A61J 1/1493* (2013.01); *A61J 1/10* (2013.01); *A61J 1/1475* (2013.01); *B65D 77/06* (2013.01);
(Continued)

(58) Field of Classification Search
CPC ......... A61J 1/10; A61J 1/1475; A61J 1/1493; A61J 1/1468; A61J 1/05; A61J 1/2003;
(Continued)

(56) References Cited

U.S. PATENT DOCUMENTS

| 6,076,457 A | 6/2000 | Vallot |
| 6,759,481 B2 | 7/2004 | Fong |

(Continued)

FOREIGN PATENT DOCUMENTS

| EP | 0276994 A2 | 8/1988 |
| EP | 0326730 A1 | 8/1989 |

(Continued)

OTHER PUBLICATIONS

International Search Report and Written Opinion of the International Searching Authority for PCT/EP2017/066384 dated Oct. 17, 2017.

(Continued)

*Primary Examiner* — Kai H Weng
(74) *Attorney, Agent, or Firm* — Heslin Rothenberg Farley and Mesiti PC; Nicholas Mesiti

(57) ABSTRACT

A pouch for transporting and/or processing a biopharmaceutical fluid, the pouch comprising a flexible wall, the flexible wall comprising a shape memory material being adapted to change shape when induced by an external stimulus, so that the pouch can be alternately in a collapsed state and in an unfolded state, the wall of the pouch in the unfolded state delimiting a closed internal cavity adapted to contain the biopharmaceutical fluid.

16 Claims, 4 Drawing Sheets

(51) Int. Cl.
*B65D 77/06* (2006.01)
*A61M 1/16* (2006.01)
*A61J 1/06* (2006.01)
*A61J 1/05* (2006.01)
*A61J 1/20* (2006.01)

(52) U.S. Cl.
CPC .................. *A61J 1/05* (2013.01); *A61J 1/067* (2013.01); *A61J 1/14* (2013.01); *A61J 1/1468* (2015.05); *A61J 1/2093* (2013.01); *A61J 2200/42* (2013.01); *A61M 1/1668* (2014.02); *A61M 2205/0266* (2013.01)

(58) Field of Classification Search
CPC ........ A61J 2200/42; A61J 1/2093; A61J 1/14; A61J 1/067; B65D 77/06; A61M 1/1668; A61M 2205/0266
See application file for complete search history.

(56) References Cited

U.S. PATENT DOCUMENTS

| | | | |
|---|---|---|---|
| 6,986,855 | B1 | 1/2006 | Hood et al. |
| 7,276,195 | B1 | 10/2007 | Fong |
| 7,422,714 | B1 | 9/2008 | Hood et al. |
| 7,690,621 | B2 | 4/2010 | Grummon |
| 2007/0010797 | A1* | 1/2007 | Nishtala ............. A61M 1/0001 604/540 |
| 2007/0034818 | A1* | 2/2007 | Grummon ............. F16K 31/025 251/129.01 |
| 2008/0302789 | A1 | 12/2008 | Stevenson |
| 2009/0069763 | A1* | 3/2009 | DiCarlo ................ A61M 27/00 604/328 |
| 2009/0281509 | A1* | 11/2009 | Gellis ..................... A61M 1/90 604/316 |
| 2011/0202031 | A1 | 8/2011 | Mihaylov et al. |
| 2012/0267388 | A1* | 10/2012 | Tom ................... B65D 83/0055 222/1 |
| 2013/0153606 | A1* | 6/2013 | Toporek ............. A61M 5/1452 222/386 |

FOREIGN PATENT DOCUMENTS

| | | |
|---|---|---|
| FR | 2781202 A1 | 1/2000 |
| FR | 3017122 A1 | 8/2015 |
| GB | 1051516 | 12/1966 |
| WO | 2005118248 A2 | 12/2005 |

OTHER PUBLICATIONS

International Preliminary Report on Patentability for International Application No. PCT/EP2017/066384 dated Jan. 8, 2019.
Extended European Search Report for European Patent Application No. 16315004.8 dated Dec. 15, 2016.

* cited by examiner

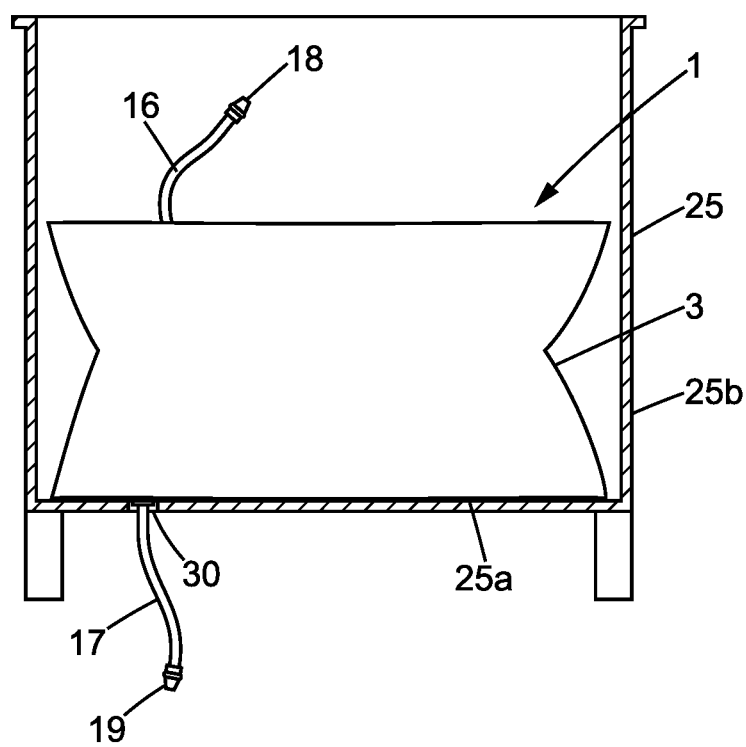
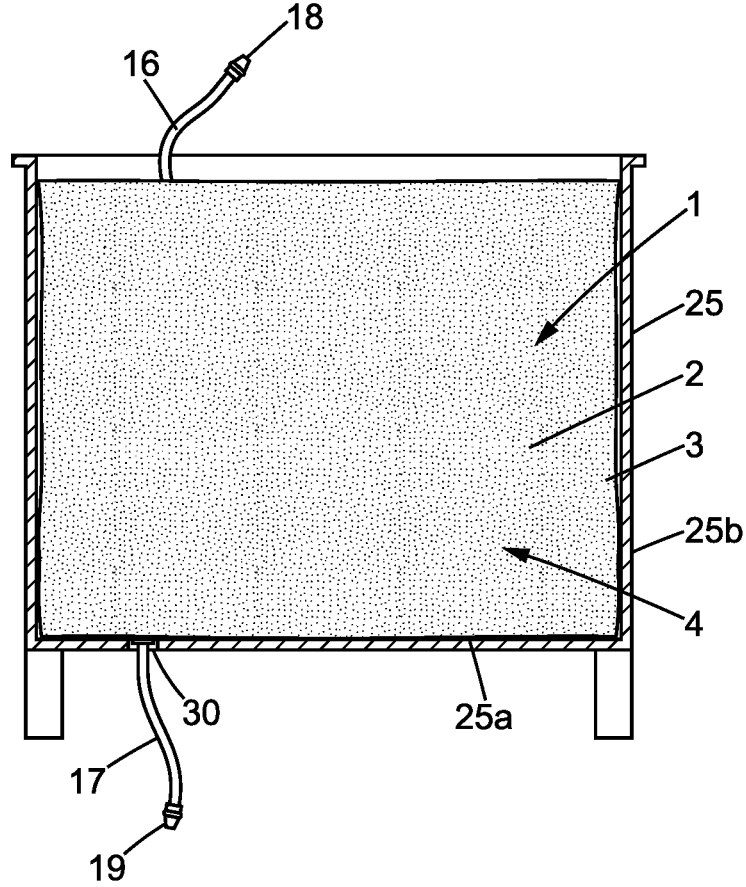

POUCH COMPRISING A SHAPE MEMORY MATERIAL TO CONTAIN A BIOPHARMACEUTICAL FLUID

CROSS REFERENCE TO RELATED APPLICATIONS

This application is a national stage filing under section 371 of International Application No. PCT/EP2017/066384, filed on Jun. 30, 2017, published in English on Jan. 11, 2018 as WO 2018/007267 A1 which claims priority to European Patent Application No. 16315004.8, filed on Jul. 7, 2016, the entire disclosure of these applications being hereby incorporated herein by reference.

BACKGROUND

The invention relates to a pouch comprising a shape memory material for receiving, processing, transporting and/or storing a biopharmaceutical fluid. The invention relates also to a system for expanding/unfolding such a pouch.

"Biopharmaceutical fluid" should be understood to mean a product derived from biotechnology (culture media, cell cultures, buffer solutions, artificial nutrition liquids, blood products and derivatives of blood products) or a pharmaceutical product or, more generally, a product intended to be used in the medical domain. Such a product is in liquid, paste or possibly powder form. The invention applies also to other products subject to similar requirements with regard to their packaging.

It is known practice to use flexible plastic pouches with large capacities to transport fluids used in the industry. Such pouches can be in two states, folded or unfolded. In the folded state, the pouch is laid flat and has a minimal volume, whereas in the unfolded state, the pouch is expanded.

When filled with a biopharmaceutical fluid, such a pouch is to be placed in a rigid container. This container maintains the pouch and makes it possible to transport the pouch over great distances, by ship or by aeroplane, from the place where the pouch has been filled to the place where the fluid will finally be used. Since biopharmaceutical fluids are often of high financial value, even often of high value for the health of individuals since they may be used for example to manufacture medicines intended for human health, it is essential that they reach their place of destination safely and without contamination.

The pouch is usually filled with the biopharmaceutical fluid after being arranged in the container. The pouch goes from the folded to the unfolded state while being gradually filled with the biopharmaceutical fluid. Such a process is for instance described in EP 0326730, in which the pouch additionally comprises side panels.

However, unfolding and filling a pouch with a fluid at the same time is a delicate operation. The flexibility of the pouch can lead to some problems, such as an improper unfolding or a restriction of the full deployment of the volume of the pouch. This may lead to a tear of the pouch and consequently to a loss of biopharmaceutical product, or to a reduced volume capacity of the pouch. This step of unfolding the pouch therefore usually requires human supervision to make sure that this operation takes place in a correct manner.

SUMMARY OF THE INVENTION

Consequently, there is, in the specific field of the invention, the need to obtain a pouch which can be easily and safely alternately folded and unfolded.

To remedy the abovementioned problem, according to a first aspect, the invention relates to a pouch for transporting and/or processing a biopharmaceutical fluid, the pouch comprising a flexible wall, the flexible wall comprising a shape memory material being adapted to change shape when induced by an external stimulus, so that the pouch can be alternately in a collapsed state and in an unfolded state, the wall of the pouch in the unfolded state delimiting a closed internal cavity adapted to contain the biopharmaceutical fluid.

Thanks to the shape memory material, the pouch can be, at least partially, unfolded before filling the pouch with the biopharmaceutical fluid. This permits to prevent any improper unfolding of the wall of pouch.

In various embodiments according to the present invention, use may also possibly be made of one and/or the other of the following dispositions, taken separately or in combination, according to which:

The pouch is a 3D pouch comprising two walls and at least one lateral gusset;

The pouch is a 2D pouch comprising two walls sealed to one another along a circumferential seam;

The pouch comprises at least one filling and/or draining orifice connected with the internal cavity, a filling and/or tube being associated respectively by a leak-tight link with the filling and/or draining orifice;

the wall comprises an inner face compatible with and/or neutral to the biopharmaceutical fluid, the inner face of the wall delimiting the closed internal cavity;

the wall comprises at least one layer of shape memory material;

the shape memory material is in the form of filaments arranged in the wall of the pouch;

the shape memory material is in a first shape when the pouch is in the collapsed state, the shape memory material being in a second shape when the pouch is in the unfolded state, the change from the first shape to the second shape of the shape memory material being induced by the external stimulus;

the shape memory material is a shape memory polymer and/or a shape memory alloy;

the shape memory material is a thermally or electrically induced shape memory material; and the pouch has when fully unfolded a capacity of between 100 litres and 1000 litres, even between 200 litres and 500 litres.

The invention also relates to a system for expanding/collapsing a pouch according to the invention, comprising the pouch and a device for expanding the pouch, the expansion device comprising a source to induce a change of the shape memory material.

The invention also relates to a method for receiving and transporting biopharmaceutical fluid, in which:

a system according to the invention is provided for expanding a pouch, the pouch being initially in the collapsed state, the pouch being arranged within a container, the expansion device induces a stimulus to change shape of the shape memory material of the wall, so that the pouch is in the unfolded state, the internal cavity of the pouch is filled with the biopharmaceutical fluid at a place of filling, notably via a filling inlet, the pouch is transported from the place of filling to a place of use of the biopharmaceutical fluid, at the place of use, the pouch is emptied of the biopharmaceutical fluid via a draining outlet, and the pouch is taken out from the container and is discarded, the pouch being disposable.

BRIEF DESCRIPTION OF THE DRAWINGS

A number of embodiments of the invention will now be described with the help of the drawings, in which:

FIG. 5 is a schematic view of the rigid container and the pouch of FIG. 4, the pouch being in a partial unfolded state and empty of biopharmaceutical fluid;

FIG. 6 is a schematic view of the rigid container and the pouch of FIGS. 4 and 5, the pouch being in a fully unfolded state and filled with biopharmaceutical fluid.

DETAILED DESCRIPTION

Below is a detailed explanation of a number of embodiments of the invention together with examples and references to the drawings. Obviously, the invention is in no way limited to the embodiment(s) described by way of nonlimiting illustration.

As illustrated of FIG. 1, the subject of the invention is a pouch 1 for receiving, transporting and/or storing a biopharmaceutical fluid 2 (said pouch 1 hereinafter being referred to as "pouch") as illustrated on FIG. 1.

The pouch 1 comprises a flexible wall 3 delimiting an internal cavity 4.

The internal cavity 4 of the pouch 1 is suited and intended to receive biopharmaceutical fluid 2.

The qualifiers "internal" or "inner", and "external" or "outer" when applied to the pouch 1 reflect the fact that the pouch 1 delimits the internal cavity 4 in which the biopharmaceutical fluid 2 is placed. It is therefore with reference to this situation that these qualifiers should be understood. The pouch 1 may take any form, notably cylindrical, parallelepipedal or other so as to form the internal cavity 4.

Figure 2A:
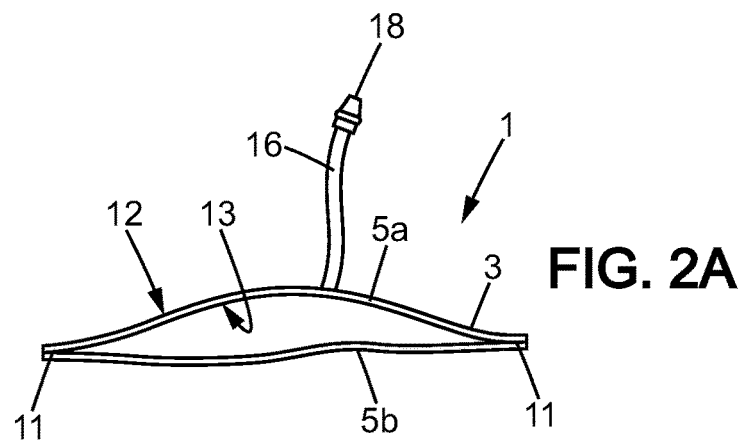
FIG. 2A and 2B are schematic cross section views along line II-II of the pouch of FIG. 1 in a collapsed state according to two different embodiments respectively in which the pouch is a 2D or a 3D pouch.

According to an embodiment illustrated on FIG. 2A, the pouch 1 may comprise two large walls 5a, 5b sealed to one another along a circumferential seam 11. Once expanded, the pouch 1 has a limited volume and remains relatively thin, which justifies the fact that the pouch 1 is often called 2D pouch (D meaning dimensions).

Figure 2B:
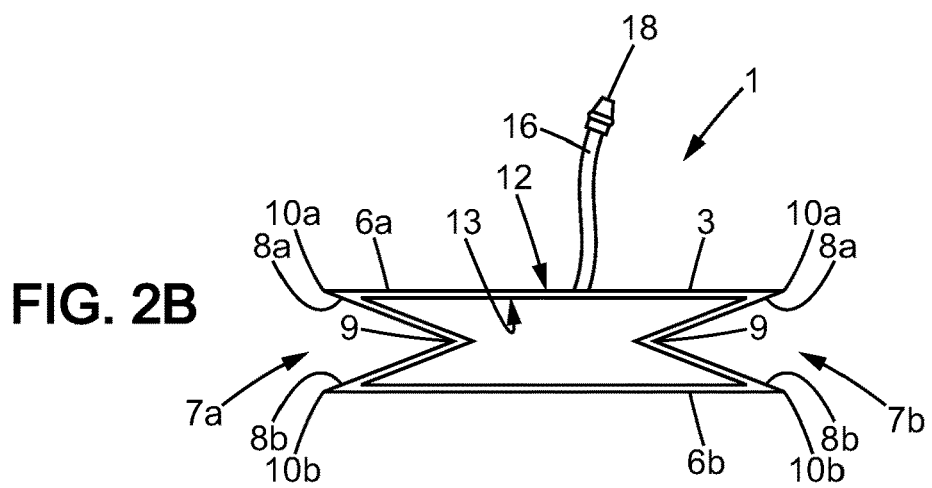

According to another embodiment illustrated on FIG. 2B, the pouch 1 may be a 3D pouch. The pouch 1 comprises two large facing walls 6a, 6b, and at least one lateral gusset with two small facing walls 8a, 8b. The pouch 1 can have two essentially analogous lateral gussets 7a, 7b. Each gusset 7 comprises two small walls 8a, 8b, connected to one another by an inner fold 9, whereas each small wall 8a, 8b is connected to the adjacent large wall 6a, 6b respectively by an outer fold 10a, 10b.

Figure 3:
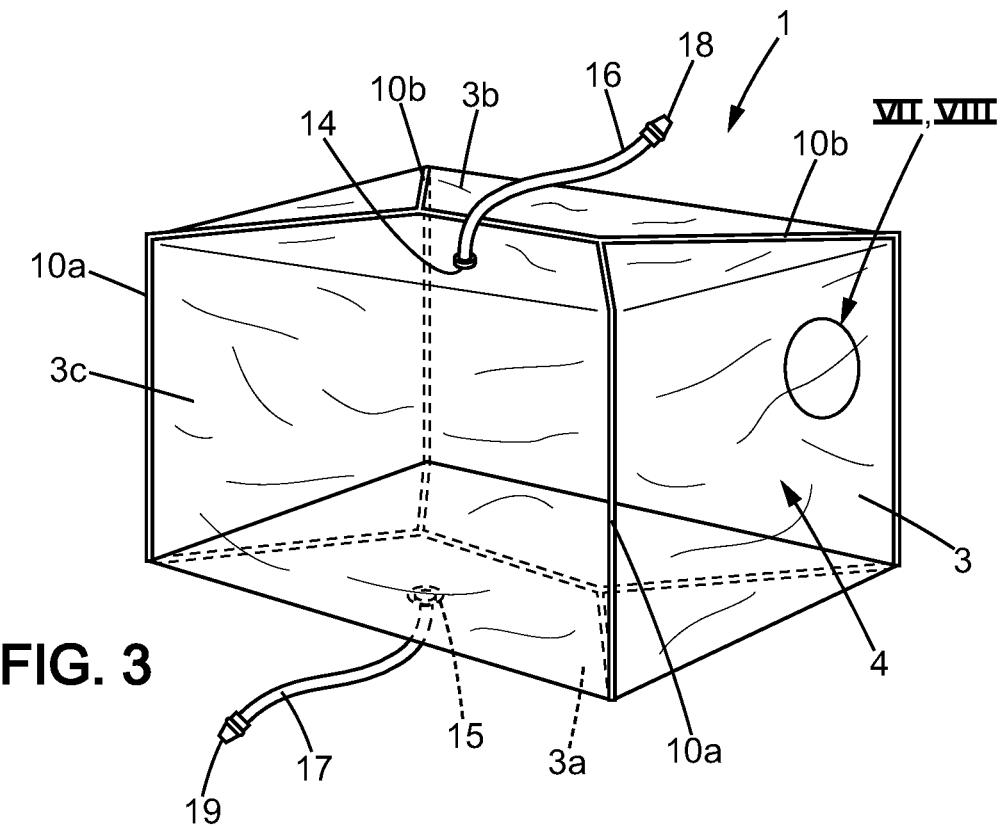
FIG. 3 is a schematic perspective view of the pouch of FIGS. 1 and 2B in a fully unfolded state.

In a fully unfolded state as visible on FIG. 3 as it will be explained below, the wall 3 comprises a bottom wall 3a, a lateral peripheral wall 3c and a top wall 3b. In the embodiment where the pouch 1 has a parallelepipedal form, the lateral peripheral wall 3c may be erected in four panels, two-by-two, at right angles or parallel to one another.

The bottom wall 3a and the top wall 3b are arranged horizontally or substantially horizontally while the lateral peripheral wall 3c is arranged vertically or substantially vertically, possibly slightly flared from the bottom wall 3a. The description is given in relation to this situation. It is also with reference to this situation that the words "horizontal", "vertical", "bottom", "top" should be understood.

The wall 3 is delimited between an outer face 12 and an inner face 13, the terms "inner" and "outer" having to be understood as explained previously. Thus, the inner face 13 delimits more particularly the internal cavity 4 of the pouch 1. The inner face 13 is neutral to and/or biocompatible with the biopharmaceutical fluid 2 which fills the pouch 1. In other words, the quality of the biopharmaceutical fluid 2 is not affected by its coming into contact with the inner face 13 of the pouch 1.

The wall 3 of the pouch 1 may be at least partly transparent or translucent so as to view through the internal cavity 4 and the biopharmaceutical fluid 2. Moreover, the wall 3 of the pouch 1 may also be at least partly, even totally, opaque to light or to ultraviolet rays, for example to ensure optimal conservation of the biopharmaceutical fluid 2, notably if the biopharmaceutical fluid 2 is a photosensitive product.

The cavity 4 is a closed and leak-tight space. "Leak-tight" should be understood here to mean that the wall 3 of the pouch 1 does not allow any passage of biopharmaceutical fluid 2, of gas, or of possible contaminants.

The pouch 1 may be provided with an orifice 14, that is to say a passage for filling with the biopharmaceutical fluid 2 and an orifice 15, that is to say a passage for emptying the biopharmaceutical fluid 2.

A tube 16 for filling the internal pouch 1 is associated with the filling orifice 14 by leak-tight links having, at the opposite end, a filling inlet 18. A draining tube 17 is associated with the draining orifice 15 having, at the opposite end, a draining outlet 19. The filling orifice 14 is more particularly located in the top wall 3b. The draining orifice 15 is more particularly situated in the bottom wall 3a or in the bottom part of the lateral peripheral wall 3c.

"Leak-tight link" should be understood to mean a structure that is already known such that the wall 3 of the pouch 1 and the tubes 16, 17 fluidically connected with the orifice 14, 15, are associated with one another in such a way as to both not allow any passage at the link between them, notably for the biopharmaceutical fluid 2 or a gas or possible contaminants. The wall 3 of the pouch 1 and the tubes 16, 17 may notably form an indissociable secure whole or be linked together by coupling systems.

"Tube" should be understood to mean a hollow structure of greater or lesser length or shortness, the term also including a simple port.

As a variant, the internal pouch 1 may comprise a single orifice for filling and for draining. According to this variant, a single tube serving as tube for filling and tube for emptying the chamber of biopharmaceutical fluid 2 is then associated by a leak-tight link with the orifice of the internal pouch 1.

According to yet another variant, the pouch 1 may comprise more than two filling and/or draining orifices, and therefore more than two filling and/or draining tubes.

The wall 3 of the pouch 1 may comprise a flexible plastic monolayer or multilayer material, made of, or comprising one or several layer of low-density polyethylene (LDPE), ethylene vinyl alcohol (EVOH), high-density polyethylene (HDPE), polyethylene (PE), polyethylene terephthalate (PET), polyamide (PA), and/or ethylene vinyl acetate (EVA). The plastic material can be heat-welded to form the pouch 1. The plastic material is biocompatible with the biopharmaceutical fluid 2.

According to the invention, the wall 3 of the pouch 1 comprises a shape memory material 20. By "shape memory material", it is understood a material that can reversibly goes from a least one shape to another shape when a predetermined external stimulus is applied.

The stimulus applied to the wall 3 to change the state of the shape memory material 20 may be of any physical or chemical type, for example, but without being limited to, a temperature change, a chemical treatment, a magnetic field, an electric current, a light radiation, etc. Once, the shape memory material 20 has taken a particular shape, this shape is said to be constant, meaning that the wall 3 remains in said shape as long as a stimulus is applied. The stimulus can be only applied temporarily to trigger a change of shape of the shape memory material 5. As a variant, the stimulus needs to be applied permanently so that the shape memory material 5 retain its shape, the material 5 returning to its initial shape as soon as the stimulus stops.

According to an embodiment, the shape memory material 20 may retain more than two shapes. According to this embodiment, the shape memory material 20 may in particular retain three shapes. For instance, a first stimulus applied to the shape memory material 20 may trigger a change from a first shape to a second shape, whereas a second stimulus may trigger a change from the second shape to a third shape of the shape memory material 20.

The shape memory material 20 may be a shape memory polymer (SMP) and/or a shape memory alloy (SMA). SMPs are polymers that derive their name from their inherent ability to return to an original permanent shape after undergoing a temporary shape deformation. SMPs can be deformed to a temporary shape by processing through heating, deformation, and finally, cooling. As long as the SMPs remain below a glass transition temperature Tg, it holds the temporary shape indefinitely. When the SMPs are heated above its transition temperature Tg, it returns to its permanent shape. It is widely known to use such shape memory polymers in various industries. For instance, such shape memory polymers are described in U.S. Pat. Nos. 6,759,481, 6,986,855, 7,276,195, 7,422,714 or WO 2005118248.

SMAS can for instance be nitinol which is a metal alloy of nickel and titanium, in particular type 60 or type 55 nitinol, Nitinol has the ability to undergo deformation at one temperature, and then recovers its original, preformed shape upon heating above a transformation temperature.

Shape memory material 20 may be arranged locally in certain part of the wall 3. For instance, only the peripheral wall 3c comprises a shape memory material 20.

Figure 7:
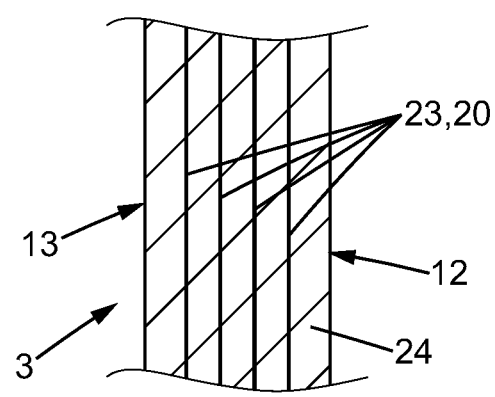
FIGS. 7 and 8 are enlarged views of the wall of the pouch of FIG. 3 according to two different arrangements of the shape memory material in the wall of the pouch respectively.

The shape memory material 20 may be arranged in filaments 23 in the wall 3. The filaments 23 can be arranged in multiple different ways, for instance parallel to each other, or overlapping with each other. The filaments 23 are advantageously made of a shape memory alloys (SMA). According to this embodiment, the filaments 23 can be also used also to conduct heat to the pouch 1 and to the biopharmaceutical fluid 2. More particularly, in the embodiment illustrated in FIG. 7, the wall 3 comprises filaments 23 of shape memory material 20 comprised or enclosed in a plastic material 24.

Figure 8:
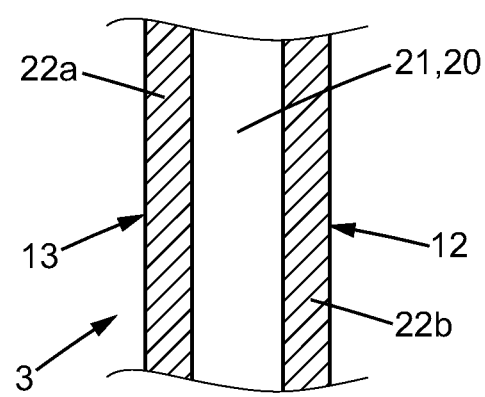

According to another embodiment represented in FIG. 8, the shape memory material 20 can be arranged as one or several layers in the wall 3 of the pouch 1 and cover, entirely or partly, the surface of the wall 3. According to one embodiment, the wall 3 may comprise a number of layers of shape memory material 20 superposed one on top of the other. Such superposed layers make it possible to obtain a good resistance of the wall 3, notably to impacts during transport operations. More particularly, according to the embodiment represented in FIG. 8, the wall 3 may comprise at least one layer 21 of shape memory material 20 and other layers 22a, 22b of plastic material.

Thanks to the shape memory material 20, the pouch 1 is suited and intended to be collapsed or unfolded/expanded. Thus, the pouch 1 may alternately be in a collapsed state or in an unfolded state.

Figure 1:
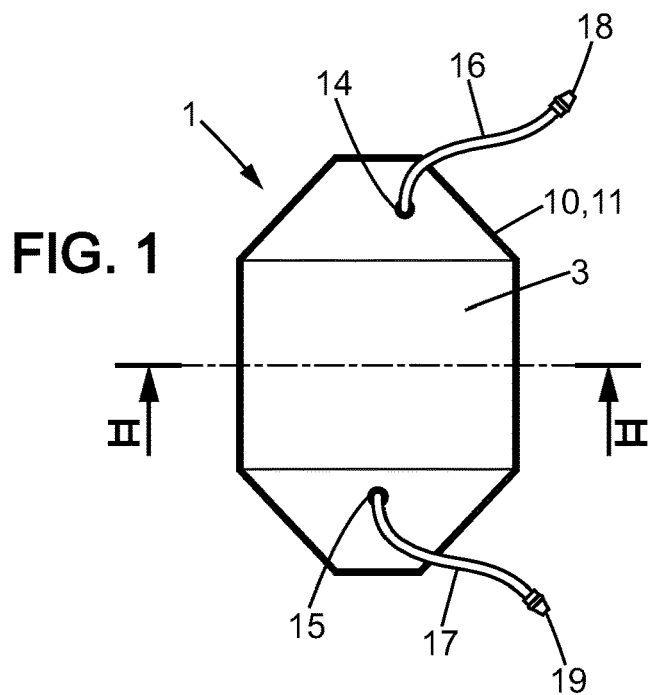
FIG. 1 is a schematic top view of a pouch in a collapsed state.
Figure 4:
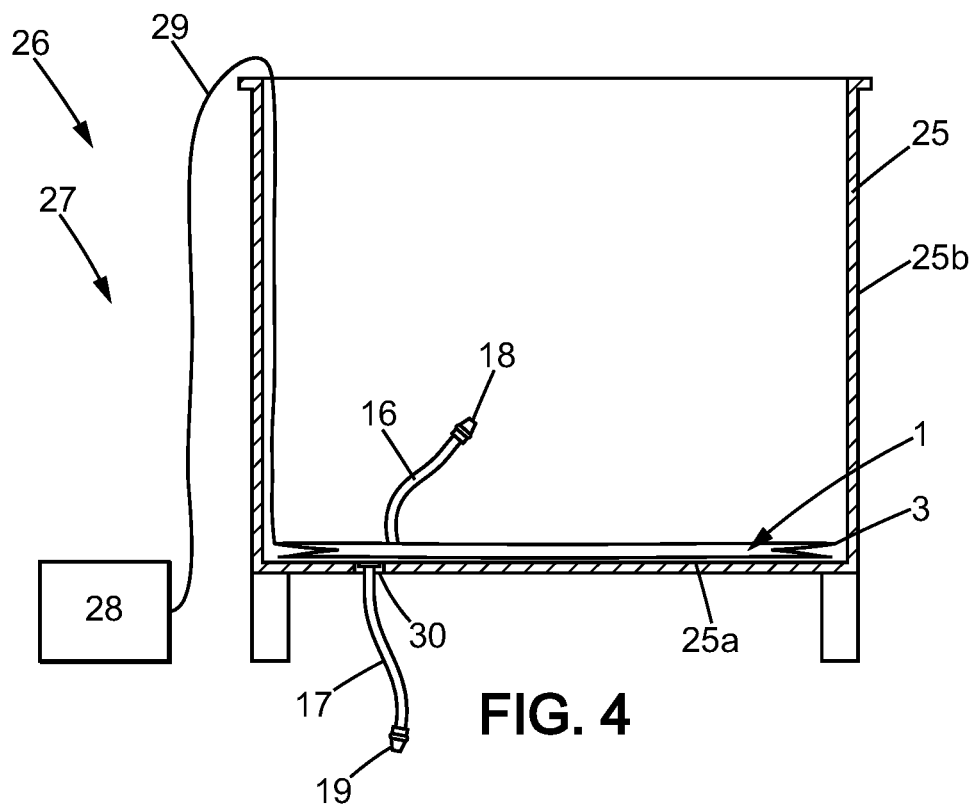
FIG. 4 is a schematic view of a pouch in the collapsed state in a rigid container.

In this collapsed state, the pouch 1 occupies a minimal space as represented in FIG. 1 or 4, and may for example be folded. In particular, the pouch 1 is substantially flat and has a small internal volume, in particular as close to zero. The shape memory material 20 is for instance in a first temporary shape.

After applying a stimulus, the shape memory material 20 comprised in the wall 3 trigger a change of shape of the pouch 1. For instance, the shape memory material 20 goes from the temporary shape to another second permanent shape. As a result, the pouch 1 goes from the collapsed state to the unfolded state. In the unfolded state, the pouch 1 is expanded in volume as represented notably in FIGS. 3 and 5. The pouch 1 then delimits the internal cavity 4 in order to contain the biopharmaceutical fluid 2.

In the unfolded state, the pouch 1 may be only partially unfolded or fully unfolded. When partially unfolded, the pouch 1 may not delimit a cavity 4 having a maximal volume capacity, and the pouch 1 may be even more unfolded to contain the biopharmaceutical fluid 2. When fully unfolded as illustrated on FIG. 3, the pouch 1 reaches its maximal volume capacity. The pouch 1 may then have a capacity of between 100 litres and 1000 litres, in particular between 200 and 500 litres, and it depends on the requirements and the applications.

Such a pouch 1 is typically designed to be combined with a rigid container 25 that contains the pouch 1 from the outside. The container 25 can have the shape of a tank, having a bottom wall 25a and a lateral wall 25b arranged vertically and transversely to the bottom wall 25a.

The container 25 is intended and suitable for receiving the pouch 1 in its entirety. Thus the pouch 1 is placed entirely within the container 25. The container 25 is preferably a rigid or semi-rigid shell. Such a container is described in a possible embodiment in the document EP1012073 and also marketed by the Sartorius Company under the trademark PALLETTANK®.

The container 25 may comprises an opening 30, so that the draining tube 17 of the pouch 1 can pass through the wall of the container 25 towards the outside.

The invention relates also to a system 26 for expanding/unfolding the pouch 1. The system 26 comprises the pouch 1 and a device 27 for expanding the pouch 1.

The expansion device 27 comprises a source of stimulus 28. The expansion device 27 can for instance be an electric source which can provide the wall 3 with an electric current to trigger a change of the shape memory material 20 of the wall 3. To this end, a line 29 can connect the source 28 to the wall 3 of the pouch 1. Alternatively, the expansion device 27 can be a heat source for instance, in the case that the shape of memory material 20 depends on temperature change as external stimulus. As explained above, other types of sources can be used according to the shape memory material 20 used of the pouch 1.

The invention relates also to a method for receiving and transporting biopharmaceutical fluid 2.

There is initially a system 26 comprising the pouch 1 and the expansion device 27. The pouch 1 is then in the collapsed state, empty of biopharmaceutical fluid 2.

As illustrated in FIG. 4, the pouch 1 in the collapsed state is first arranged in the container 25. The pouch 1 can for instance be placed in contact with the bottom 25a/and or the lateral wall 25b of the container 25.

The pouch 1 is expanded with the expansion device 27. In particular, a stimulus is provided to the wall 3 so as to the shape memory material 20 change its shape. The pouch 1 is then in the unfolded state, as visible in FIG. 5. As previously explained, in the unfolded state, the pouch 1 may not be fully unfolded but may only be in an intermediate state in which the pouch 1 is only partially unfolded. However, as a variant, the pouch 1 may be totally unfolded before being filled with biopharmaceutical fluid 2 when in the unfolded state. Thanks to the shape memory material 20, it is possible to ensure that the pouch unfolds correctly.

The internal cavity 4 of the pouch 1 is filled with biopharmaceutical fluid 2, notably via the filling inlet 18 of the pouch 1. Then the filling inlet 18 is brought to the closed state. As a result of filling the pouch 1 with the biopharmaceutical fluid 2, the wall 3 of the pouch 1 may fully unfold so that the cavity 4 of the pouch 1 reaches its maximal volume capacity. When filled with the biopharmaceutical fluid 2, the pouch occupies the inner space of the container and is advantageously supported by the bottom wall 25a and the lateral wall 25b of the container 25, as illustrated on FIG. 6.

The pouch 1 may then be separated from the expansion device 27 if the wall 3 can retain its shape after stopping inducing the stimulus. As a variant, the pouch 1 may then be separated from the expansion device 27 before being filled with the biopharmaceutical fluid 2.

The container 25 comprising the pouch 1 may be loaded onto a ship, a truck, an aeroplane in order to transport the biopharmaceutical fluid 2. These operations can extend over a rather long period, for example several months, and even several years, involving, for example, storage. The biopharmaceutical fluid 2 may also be processed after, before or during the transportation operations.

Following these operations, the pouch 1 is emptied of the biopharmaceutical fluid 2 by bringing the draining outlet 19 to the open state. The pouch 1 may thus be emptied of all of the biopharmaceutical fluid 2.

Once the biopharmaceutical fluid 2 has been transferred, the pouch 1 may be taken out of container 25. The pouch 1 may be discarded, the pouch 1 being disposable.

As a variant, the pouch 1 may be brought back to the collapsed state, for example by applying another stimulus to the wall 3 with the expansion device 27, or by stopping inducing the stimulus to the wall 3 with the expansion device 20 so that the shape memory material 5 can return to its initial shape. The pouch 1 can then be transported back to the initial place of filling. The pouch 1 may then be reused for the future transportation of another biopharmaceutical fluid 2.

The method described above may be carried out partially, the steps described above being able to be carried out independently of one another.

Obviously, the invention is not limited to the embodiments described previously and given purely by way of example. It encompasses a wide range of modifications, alternative forms and other variants that a person skilled in the art will be able to envisage within the scope of the present invention and notably all combinations of the different modes of operation described previously, being able to be taken separately or together.

The invention claimed is:

1. A system for expanding and/or collapsing a pouch for transporting and/or processing a biopharmaceutical fluid, comprising:
   the pouch comprising a flexible wall, the flexible wall comprising a shape memory material and a second material that differs from shape memory material, the shape memory material being adapted to change shape when induced by an application of an external stimulus to the shape memory material such that the shape memory material changes the configuration of the pouch between a collapsed folded state and an unfolded state, the flexible wall of the pouch delimiting a closed internal cavity adapted to contain the biopharmaceutical fluid; and
   an expansion device that is configured to provide said external stimulus to the shape memory material of the flexible wall external to the internal cavity to change shape of the pouch from the collapsed state to the unfolded state, and
   wherein the pouch further comprises at least one filling and/or draining tube that is in communication with the internal cavity, and wherein the expansion device is coupled to the flexible wall via a line, that is separate and distinct from the at least one filling and/or draining tube, that applies the external stimulus to the shape memory material external to the internal cavity.

2. The system according to claim 1, wherein the pouch comprises a 3D pouch comprising two flexible walls and at least one lateral gusset.

3. The system according to claim 1, wherein the pouch comprises a 2D pouch comprising two flexible walls sealed to one another along a circumferential seam.

4. The system according to claim 1, wherein the pouch further comprises at least one filling and/or draining orifice connected with the internal cavity, and a filling and/or draining tube being associated respectively by a leak-tight link with the filling and/or draining orifice.

5. The system according to claim 1, wherein the flexible wall comprises an inner face compatible with and/or neutral to the biopharmaceutical fluid, the inner face of the flexible wall delimiting the closed internal cavity.

6. The system according to claim 1, wherein the flexible wall comprises at least one layer of the shape memory material and at least one layer of the second material that are overlapping.

7. The system according to claim 1, wherein the shape memory material is in the form of filaments arranged in the flexible wall of the pouch.

8. The system according to claim 1, wherein the shape memory material is in a first shape when the pouch is in the collapsed folded state, and in a second shape that differs from the first shape when the pouch is in the unfolded state, the change from the first shape to the second shape of the shape memory material being induced by the application of the external stimulus.

9. The system according to claim 1, wherein the shape memory material is a shape memory polymer and/or a shape memory alloy.

10. The system according to claim 1, wherein the shape memory material is configured such that the external stimulus is a thermal stimulus comprising a temperature change or an electrical stimulus comprising an electrical current.

11. The system according to claim 1, wherein, when the pouch is fully unfolded, the pouch has a capacity of between 100 litres and 1000 litres.

12. The system of claim 1, wherein the internal cavity of the pouch contains the biopharmaceutical fluid, and wherein the biopharmaceutical fluid is in a liquid, paste or powder form.

13. The system of claim 12, wherein the biopharmaceutical fluid contacts the flexible wall.

14. The system of claim 1, wherein the second material is a plastic material.

15. The system of claim 1, wherein the shape memory material is configured such that the shape memory material changes from a first shape to a second particular shape when the external stimulus is applied thereto, and remains in the second particular shape after the application of the external stimulus has ceased.

16. The system of claim 5, wherein the second material forms the inner face of the flexible wall.

* * * * *